United States Patent [19]

Fearnot et al.

[11] Patent Number: 4,985,022
[45] Date of Patent: Jan. 15, 1991

[54] CATHETER HAVING DURABLE AND FLEXIBLE SEGMENTS

[75] Inventors: Neal E. Fearnot, West Lafayette; Melvin K. Hawkins, Bloomington; Richard B. Sisken, West Lafayette, all of Ind.

[73] Assignees: MED Institute, Inc., West Lafayette; Cook Incorporated, Bloomington, both of Ind.

[21] Appl. No.: 275,435

[22] Filed: Nov. 23, 1988

[51] Int. Cl.$^5$ .............................................. A61M 25/00
[52] U.S. Cl. ..................................... 604/282; 604/280
[58] Field of Search ....................... 604/282, 280, 93; 128/656–658, 348.1

[56] References Cited

U.S. PATENT DOCUMENTS

| | | | |
|---|---|---|---|
| 4,368,730 | 1/1983 | Sharrock | 604/282 |
| 4,385,635 | 5/1983 | Ruiz | 604/280 |
| 4,547,192 | 10/1985 | Brodsky et al. | 604/282 |
| 4,596,563 | 6/1986 | Pande | 604/280 |
| 4,784,639 | 11/1988 | Patel | 128/658 |

OTHER PUBLICATIONS

"Introducing the Arrow Theracath TM Spring Wire Reinforced Continuous Epidural Catheter," Arrow International, Inc., May 1986.

*Primary Examiner*—Stephen C. Pellegrino

[57] ABSTRACT

An epidural catheter is disclosed having a durable and a flexible segment joined together. The flexible segment is inserted into a patient with the use of a well-known needle which is removed by passing the needle over the outside of the catheter. The flexible segment is atraumatic to the surrounding tissue. The flexible segment includes a plastic tube surrounded by a wire coil for pushing the tube into a passageway of the tissue. The distal end of the plastic tube and wire coil are joined to prevent unwinding of the coil when extracted. The tightly coupled wire coil also permits the flexible portion to be easily inserted into the passageway of the tissue. The durable segment joined to the flexible segment includes a stainless steel tube with a flat wire coil surrounding a length of the tube. The stainless steel tube permits fluid at an elevated pressure to pass through the hollow passageway therein without rupturing. The flat wire coil prevents kinking of the semi-rigid stainless steel tube. When a fluid at an elevated pressure is received, the distal end of the flexible tube is closed to diffuse the fluid passing through the length of the catheter. Slits are provided laterally on the side of the plastic tube for emitting and diffusing the fluid through the wire coil.

33 Claims, 3 Drawing Sheets

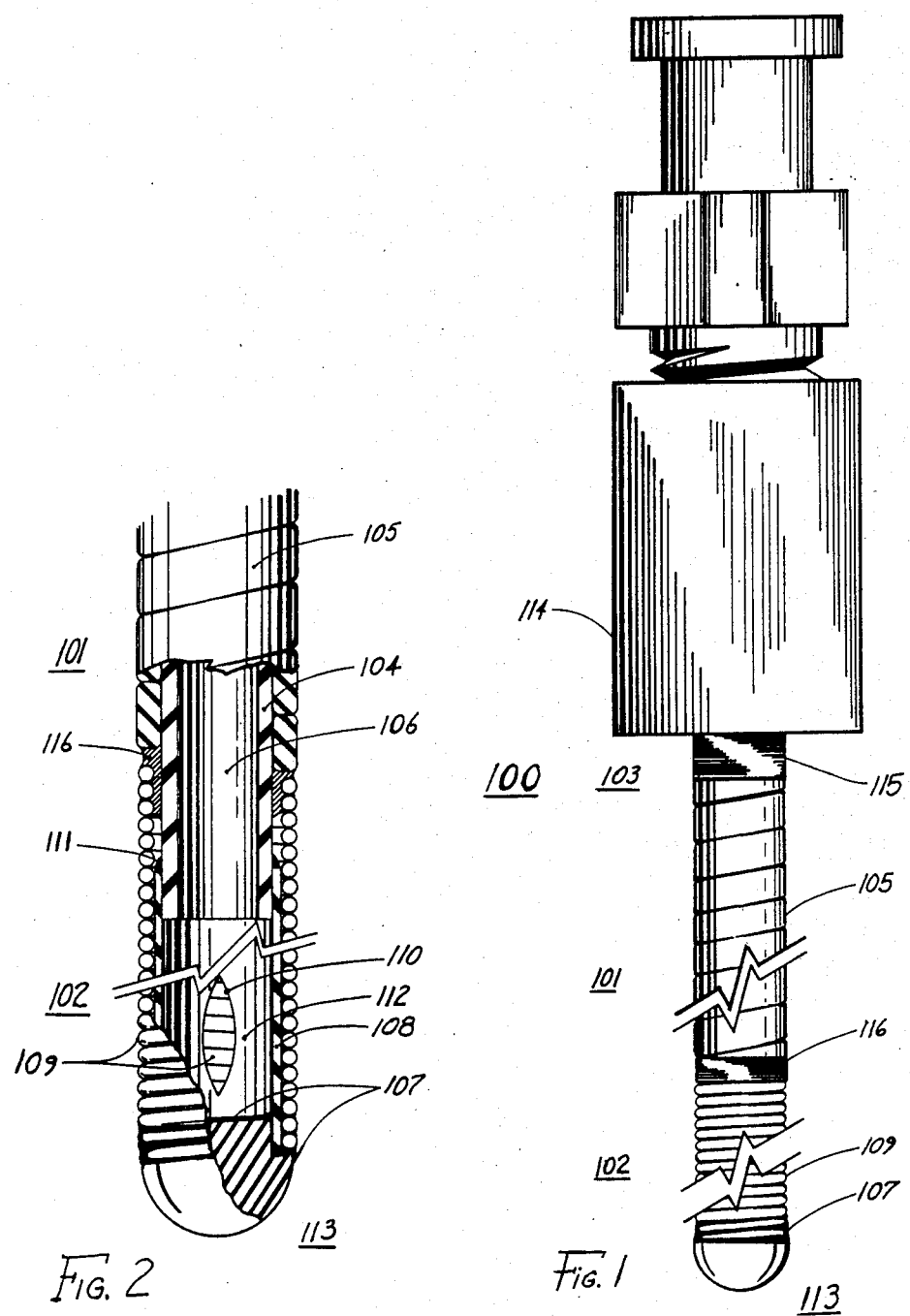

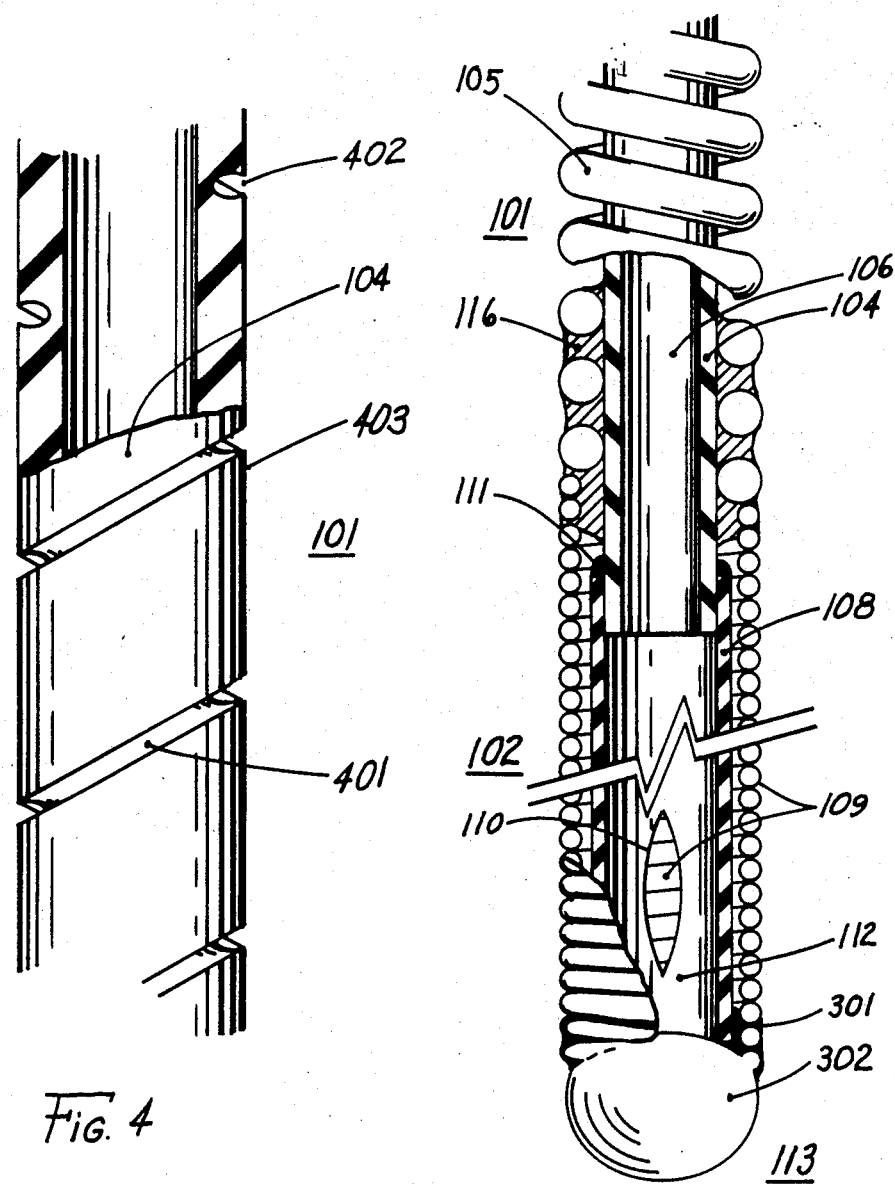

CATHETER HAVING DURABLE AND FLEXIBLE SEGMENTS

TECHNICAL FIELD

This invention relates to catheters and, in particular, catheters having at least two segments.

BACKGROUND OF THE INVENTION

Catheters of various types and sizes have been used by physicians extensively. One use of the catheter is in providing regional anesthesia which produces profound analgesia with minimal physiologic alterations. When used at the start of an operation, regional anesthesia minimizes the total dosage of inhalation or intravenous anesthetic drugs required, hastens awakening, and permits early ambulation. When administered at the conclusion of surgery, regional anaesthesia produces postoperative analgesia with reduced risk of respiratory depression. Furthermore, certain types of pain are difficult to treat with systemic narcotics. For example, a bladder spasm following genitourinary surgery may be exacerbated by systemic opioids but is easily treated with a caudal epidural block. When prolonged analgesia is required, a catheter is inserted into the caudal or lumbar epidural space to provide intermittent or continuous injections of local anesthetics.

Caudal epidural anesthesia is notable for its simplicity, safety, and effectiveness and is one of the most frequently used regional anesthetic techniques for operations below the diaphragm in children.

When continuous pain relief is desired, the only equipment presently available is either a 19 or 20 gauge epidural catheter which is passed through either a 17 gauge Tuohy or an 18 gauge Crawford needle. Designed specifically for adults, these needles are approximately 3½" long and have an outside diameter ranging from 0.050" to 0.059" along with an inside diameter ranging from 0.33" to 0.041". However, these needles are extraordinarily cumbersome to use in children, since the distance from the skin to the epidural space is only 10–15 mm. Obviously, smaller needles and catheters are desirable.

Continuous lumbar epidural anesthesia is a well-established and accepted technique in adult patients. It differs from caudal epidural anesthesia by the location where the needle is inserted. A lumbar approach has several advantages over the caudal epidural technique. However, the lumbar approach has more problems as well. First, placement of a lumbar epidural needle is technically more difficult than placing a needle into the caudal epidural space, particularly with the 17 and 18 gauge equipment presently available for use. Second, there is a greater risk of unintentionally puncturing the dura. This is commonly known as an unintentional spinal tap with the possibility of severe headaches depending on the size of the dural puncture hole. The smaller the hole, the less likely a headache. Obviously, a 17 or 18 gauge hole in the dura is much more likely to cause a severe headache than a 22 or 23 gauge puncture hole.

The smallest presently offered epidural catheter is a 20 gauge continuous epidural catheter with an outside diameter of approximately 0.035". This catheter is constructed of a spring wire guide coated with a plastic material. The distal end of the spring wire guide appears to have been stretched to allow the plastic material to form in between the stretched windings. This catheter is advertised as kink-resistant, but is still kinkable particularly when a patient would bend or collapse the catheter by laying on or twisting the body of the catheter outside the insertion site.

Since the plastic material is coated over the spring wire guide, the coating appears to have fluid pressure limitations as well as being susceptible to being easily ruptured.

Another problem associated with the distal end of the catheter is that of tissue ingrowth. Here, tissue is allowed to grow within or between the winding coils of the distal tip. The elastic distal spring tip is also susceptible to uncoiling when the catheter is removed from the patient. This causes trauma to the insertion site as well as possible injury to the dura.

SUMMARY OF THE INVENTION

The foregoing problems are solved and a technical advance is achieved in an illustrative catheter having both a durable segment for withstanding abusive environments external to the patient and a flexible segment for atraumatic insertion and extraction from patient tissue. The durable segment comprises, for example, a stainless steel metal tube having a hollow passageway for transporting fluids between the distal and proximal ends. The stainless steel metal tube advantageously permits the transportation of fluids entering at pressures in excess of 2,000 psi. This represents a significant advantage over the plastic coated spring wire guide catheter in which fluid pressures are limited without rupturing the plastic coating. The flexible segment is atraumatic to tissue and is pushable through a passageway in tissue for transporting fluid from the durable segment to the tissue. The flexible segment illustratively comprises a plastic tube such as polyimide, which is joined with the durable segment. The flexible segment also includes a wire coil surrounding the plastic tube for pushing the flexible segment through a passageway in selected tissue. Advantageously, the distal ends of the wire coil and plastic tube are joined together for preventing the wire coil from uncoiling when extracted and for pushing the flexible segment into the passageway of the tissue during insertion. The windings of the wire coil are tightly coupled to prevent compression and extension during insertion and extraction, respectively.

In one illustrative embodiment, material is also applied to close the distal end of the flexible segment. Openings are slit or formed in the length of the plastic tube to diffuse the emission of fluid being transported therein. Otherwise, fluid at an elevated pressure would be emitted from the distal end causing possible injury to the surrounding tissue. By emitting the fluid along the length of the plastic tube, fluid is further diffused through the wire coil to the surrounding tissue. Materials such as medical grade epoxy are used to both close the distal end of the plastic tube and form a smooth-surfaced or rounded tip thereat.

In a second embodiment, a smooth-surfaced or rounded tip of stainless steel metal is attached or formed at the distal end of the flexible segment to facilitate insertion of the catheter into a passageway in tissue without causing trauma to the tissue. A medical grade adhesive secures the distal ends of the plastic tube and wire coil together.

In a third embodiment for low or minimal pressure fluids at the tip of the catheter, the distal end of the plastic tube is left open for emitting the fluid. The rounded tip is formed by soldering and forming the distal end windings of the wire coil. A medical grade adhesive secures the formed tip to the distal end of the plastic tube.

To virtually eliminate kinking of the stainless steel tube when bent, a coil of flat wire surrounds the stainless steel tube. Alternatively, a round wire tightly wrapped around the metal tube or a spiral trench formed in the tube also advantageously prevents kinking of the tube.

The durable and flexible segments are joined together such as by inserting the proximal end of the plastic tube over the distal end of the stainless steel tube and using, for example, a medical grade adhesive for bonding the two ends together.

The proximal end of the wire coil surrounding the flexible segment is also advantageously joined to the distal end of the metal tube to further prevent expansion and compression of the wire coil. A material such as solder affixes the flat and round wire coils at the proximal end of the stainless steel tube.

When the two segments are joined, a catheter is formed which is passable through very small apertures having diameters less than 0.035". Presently, catheters of the present invention are capable of going through 26 gauge thin-wall needles with inside diameters of only 0.012". Catheters of this small size, which are capable of passing sufficient volumes of fluid, represent a significant departure in the art.

BRIEF DESCRIPTION OF THE DRAWING

FIG. 1 depicts a catheter including a flexible segment and a durable segment;

FIG. 2 depicts a cross-section of the flexible segment and the distal end of the durable segment of FIG. 1;

FIG. 3 depicts a second embodiment of the durable and flexible segments of FIG. 2;

FIG. 4 depicts a third embodiment of the durable segment of FIG. 2; and

DETAILED DESCRIPTION

Figure 5:
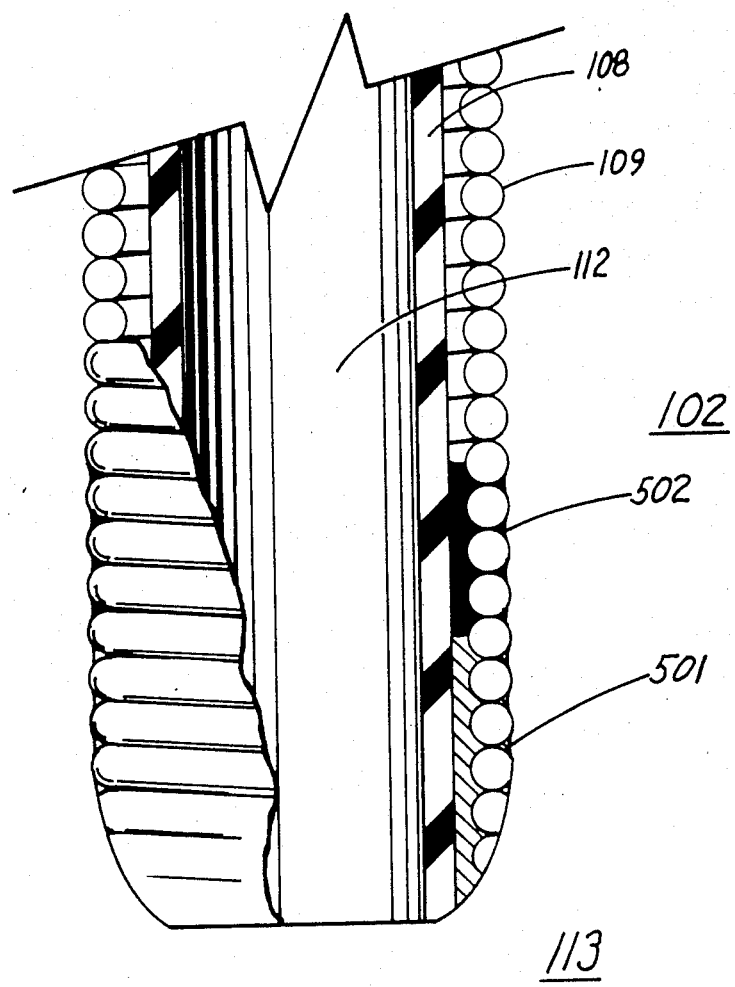
FIG. 5 depicts a third embodiment of the flexible segment of FIG. 2.

Depicted in FIG. 1 is an illustrative epidural catheter 100 having a durable elongated segment 101 and a flexible elongated segment 102 which is passable through an aperture having a diameter less than 0.035". Presently, catheters can be fabricated with outside diameters as small as 0.012" for insertion through a 26-gauge thin-wall Tuohy or Crawford needle. A caudal epidural catheter is inserted at the sacro-coccygeal ligament. A lumbar epidural catheter is inserted at another position of the spine such as the posterior superior iliac crest. When the needle is inserted, the epidural catheter is inserted through the hollow passageway of the needle into the tissue. When the catheter is in place, the needle is removed over the entire length of the catheter, and a well-known and commercially available medical grade connector 114, such as a Tuohy-Borst connector, which is available from Cook, Inc., is attached to the proximal end 103 of the catheter.

A cross-sectional view of the flexible segment 102 and the distal end of durable segment 101 of the catheter is depicted in FIG. 2. Durable segment 101 of the catheter includes a stainless steel tube 104, commonly known as a cannula. In this preferred illustrative embodiment, the outside diameter of the catheter is nominally 0.020" and passable through an aperture having a diameter no greater than 0.022". The stainless steel cannula is commercially available stainless steel tubing having an outside diameter of 0.014"±0.0005" and an inside diameter of 0.009"±0.0005". Stainless steel tubing such as this is available from the K-Tube Corporation. As a consequence of the metal tube, fluids may enter the proximal end of hollow passageway 106 of the durable segment at pressures in excess of 2,000 psi. Commonly available medical grade connectors typically limit the pressure at which the fluid can be applied. This essentially nonkinkable durable segment is placed outside and next to the body of a patient without concern for crushing or rupturing the segment due to bending or the patient laying on the durable segment. In addition, a stainless steel tube offers corrosion resistance to body fluids and other substances externally applied.

Coiled in a spiral configuration surrounding the stainless steel cannula is wire 105. Wire 105 is inserted over or wrapped around cannula 104 to prevent kinking when the stainless steel tube is bent.

In this embodiment, flat wire 105 has a rectangular cross-sectional shape with a 0.008" width and a 0.003" height and is wound into a coil having a 0.020" outside diameter. Such a coil is commercially available from Cook, Inc. The wire coil is inserted over the cannula.

Depicted in FIG. 3 is a second illustrative embodiment of the flexible segment 102 and the distal end of durable segment 101. In this second illustrative embodiment, wire 105 is round 0.004" diameter wire that is tightly wrapped around cannula 104. Wire 105 is wrapped to that the resultant coil does not slide appreciably when the cannula is bent. Here, cannula 104 has an outside diameter of 0.010" and an inside diameter of 0.007". As a result, the overall combined diameter of durable segment 101 is approximately 0.018". Wire 105 may be wrapped from a single strand of wire or from a tightly coupled wire coil having a 0.015" outside diameter. Such a coil is, again, commercially available from Cook, Inc.

A third illustrative embodiment of durable segment 101 is depicted in FIG. 4. In this third embodiment, cannula 104 comprises a commercially available stainless steel tube having a 0.020" outside diameter and a 0.010" inside diameter with a spiral trench 401 formed therein. Adjacent windings of the trench are spaced approximately 0.020" apart. The depth of the trench is approximately 0.003" with the opening 402 at the outside surface 403 of the cannula being approximately 0.002". The trench is ovally shaped without any sharp discontinuities, such as corners or grooves, to minimize cracks or tears in the cannula when bent. The spiral trench distributes the forces along the length of the cannula when bent to prevent kinking of the tube. The spiral trench is formed in a stainless steel tube by any one of a number of well-known techniques depending on the exact shape of the trench that is desired. Such an embodiment lends itself to less labor intensive manufacture.

Returning the reader's attention to FIGS. 1 and 2, flexible segment 102 comprises a plastic tube 108 surrounded by tightly coupled wire coil 109. Plastic tube 108 has a nominal inside diameter of 0.0142" with a nominal wall thickness of 0.0010". As a result, the plastic tube nominally has an outside diameter of 0.0162". In the illustrative embodiment, the plastic tube has an overall length of just over 8 cm. The plastic tubing comprises a polyimide tubing such as is available from Micro ML Tubing Sales. This tubing comprises a flexible, non-flammable, radiation resistant, and non-corrosive material. In addition, any apertures or openings such as slit 110 are resistant to tearing.

Wire coil 109 includes 0.002" diameter wire with the windings tightly coupled together with very little, if any, spacing therebetween. The outside diameter of wire coil 109 is nominally 0.020". Such wire coil is commercially available from Cook, Inc., as well as other suppliers.

The proximal end of the plastic tube is inserted over approximately 2 mm of the distal end of stainless steel tube 104.

Adhesive material 111, such as a medical grade adhesive, is applied to the proximal end of plastic tube 108 and the distal end of stainless steel tube 104 to more firmly position and join the two ends together. A medical grade adhesive, such as formula FMD-13 from the Loctite Corporation, is just one suitable adhesive material for use with this catheter.

After the plastic tube and cannula are joined, wire coil 109 is positioned over and surrounds the plastic tube and cannula as shown. The proximal end of the wire coil 109 and the distal end of flat wire 105 are attached to stainless steel tube 104 using, for example, a solder material 116 at a distance from adhesive material 111.

Plastic tube 108 further comprises a hollow passageway 112 for transporting fluid from passageway 106 of the durable segment to surrounding tissue when positioned therein. To prevent injury to the dura or other surrounding tissue when fluid at an elevated pressure is received, the distal end of the plastic tube is closed with a medical grade epoxy 107. Dexter Hysol casting compound CH-W795 and hardener HW-796 is a commercially available medical grade epoxy. Closing of the distal end of the plastic tube prevents fluid passing through the hollow passageways of the catheter from being emitted at an elevated pressure level. Slits such as 110 are made on opposite sides of the plastic tube laterally parallel to the longitudinal axis thereof for emitting and diffusing the fluid. The tightly coupled windings of wire coil 109 further diffuse the fluid being emitted from the slits at the distal end of the catheter.

Epoxy material 107 is also used to join wire coil 109 to plastic tube 108. This prevents wire coil 109 from unwindinq when extracted from a tissue passageway. The joining of the two distal ends also permits flexible segment 102 to be pushed into the passageway of an inserting needle.

To prevent injury or trauma to surrounding tissue, the distal end of the catheter includes a rounded or smooth-surfaced tip 113 formed or attached to the distal end of the wire coil and/or plastic tube. As shown in FIG. 2, tip 113 is formed from the epoxy material 107 closing the end of hollow passageway 112 of the plastic tube. After the distal end of the plastic tube is dipped into the epoxy material, the epoxy material is allowed to dry, and tip 113 is formed into a rounded surface using any one of a number of well-known techniques.

As shown in FIG. 3, tip 113 in the second illustrative embodiment comprises a metal material 302 which is formed at the distal end of the flexible segment by, for example, welding a stainless steel material to wire coil 109. The distal ends of wire coil 109 and plastic tube 108 are joined by an adhesive material 301 such as well-known and commercially available superglue.

Depicted in FIG. 5 is a third illustrative embodiment of the distal end of flexible segment 102. In this embodiment, the distal end of plastic tube 108 is left open for emitting the fluid when the fluid is received at minimal or low pressure levels that are atraumatic to tissue. Tip 113 is formed by applying a solder material 501 to the distal end windings of wire coil 109 and grinding, buffing, and/or polishing the distal end into a smooth or rounded surface. The distal end of the wire coil is secured to plastic tube 108 with medical grade adhesive 502. Slit 110 is not required in this third embodiment.

As previously described with respect to FIG. 1, connector 114 is attached to proximal end 103 of the catheter. This connector is then, in turn, connectable to a number of sources for receiving fluid into the catheter at appropriate pressure levels via standard medical Luer fittings. A solder material 115 is also applied to proximal end 103 of the catheter to fixedly position wire 105 to stainless steel tube 104.

This two segment catheter having both a flexible and a durable segment permits continuous long term application of anesthetics or analgesics. Flexible segment 102 is atraumatic to the surrounding tissue. However, durable segment 101 permits continued abusive use without kinking or rupturing. The stainless steel metal also affords a noncorrosive environment.

It is to be understood that the above-described catheter is merely an illustrative embodiment describing the principles of this invention and that other catheters may be devised by those in the art without departing from the spirit and scope of this invention. In particular, this catheter includes a metal cannula surrounded by a wire for providing extraordinary strength for high pressure fluids without kinking. Other such metals and wraps of other materials may also be used. The flexible segment consisting of a plastic tube may be comprised of other flexible materials having a hollow passageway therethrough. A safety wire may also be attached between the proximal and distal ends of the catheter to guard against unexpected material failure.

What is claimed is:

1. A catheter comprising:
   a durable elongated segment having a distal and a proximal end and a hollow passageway therebetween;
   a more flexible elongated segment having a distal and a proximal end and a hollow passageway therebetween, said proximal end of said flexible segment and said distal end of said durable segment being joined together; and
   a wire coil surrounding said flexible segment and being joined to said flexible segment at said distal end thereof.

2. The catheter of claim 1 further comprising a wire wrapped around said durable segment.

3. The catheter of claim 1 further comprising a wire coil surrounding said durable segment.

4. The catheter of claim 1 wherein said durable segment includes a trench formed in an outside surface thereof.

5. The catheter of claim 1 wherein said catheter includes dimensions for passing through an aperture less than 0.035" in diameter.

6. The catheter of claim 1 wherein said durable segment includes a metal tube.

7. The catheter of claim 1 wherein said flexible segment comprises a plastic tube.

8. The catheter of claim 7 wherein said plastic tube comprises polyimide.

9. The catheter of claim 1 further comprising a material for closing said hollow passageway at said distal end of said flexible elongated segment.

10. The catheter of claim 9 wherein a length of said flexible segment includes an opening from said hollow passageway thereof.

11. The catheter of claim 10 wherein said tip is formed from a medical grade epoxy material.

12. The catheter of claim 10 wherein said tip comprises metal affixed to said wire coil.

13. The catheter of claim 1 wherein said flexible segment includes a tip at said distal end thereof.

14. An epidural catheter for passing through an opening less than 0.035" in diameter comprising:
   a semi-rigid stainless steel tube;
   a first wire coil surrounding a length of said stainless steel tube;
   a flexible plastic tube having a proximal end joined with a distal end of said stainless steel tube; and
   a second wire coil surrounding said flexible plastic tube having a distal end joined to a distal end of said plastic tube.

15. The catheter of claim 14 further comprising a rounded tip at said distal ends of said plastic tube and said second coil.

16. A catheter comprising:
   durable means for transporting a fluid; and
   more flexible means joined to said durable means and having a rounded distal end for atraumatic insertion in tissue and including elongated means for transporting said fluid from said durable means to said tissue and coil means positioned about and joined with said elongated means for pushing said rounded distal end through a passageway in said tissue.

17. The catheter of claim 16 wherein said durable means comprises elongated means having a passageway therein for transporting said fluid and means about an outer surface of said elongated means for preventing kinking of said elongated means.

18. The catheter of claim 17 wherein said elongated means comprises a metal tube and said means for preventing kinking comprises a wire coil surrounding a length of said metal tube.

19. The catheter of claim 17 wherein said means for preventing kinking comprises a wire wrapped about a length of said elongated means.

20. The catheter of claim 17 wherein said means for preventing kinking comprises a trench formed about a length of said outer surface of said elongated means.

21. The catheter of claim 16 wherein said elongated means includes a passageway therein for transporting said fluid and wherein said coil means surrounds said elongated means and is joined therewith at a distal end of said elongated means for pushing said elongated means into said passageway in said tissue.

22. The catheter of claim 21 wherein said elongated means comprises a plastic tube and said coil means comprises a wire coil surrounding a length of said plastic tube and joined at a distal end thereof.

23. The catheter of claim 22 further comprising means for closing said distal end of said plastic tube.

24. The catheter of claim 22 further comprising means for joining the distal ends of said plastic tube and said wire coil together.

25. The catheter of claim 24 further comprising an opening along said length of said plastic tube for emitting said fluid.

26. The catheter of claim 22 further comprising means at the distal end of at least one of said plastic tube and said wire coil for pushing said flexible means atraumatically into said tissue.

27. A catheter comprising:
   a durable segment having a hollow passageway for transporting a fluid; and
   a more flexible segment including an elongated member having a hollow passageway joined with said durable segment and insertable in a passageway in tissue for transporting said fluid from said durable segment to said tissue; said flexible segment including an elongated member and a wire coil positioned longitudinally thereabout and joined therewith for inserting said flexible segment into said passageway in said tissue.

28. The catheter of claim 27 wherein said durable segment includes a trench formed therein.

29. The catheter of claim 27 wherein said elongated member includes a plastic tube having a hollow passageway for transporting said fluid from said hollow passageway of said durable segment to said passageway in said tissue.

30. The catheter of claim 29 wherein said flexible segment includes a material for closing a distal end of said hollow passageway of said plastic tube.

31. The catheter of claim 30 wherein said plastic tube includes an opening along a length thereof for emitting said fluid.

32. The catheter of claim 27 further comprising a wire wrapped around said durable segment.

33. The catheter of claim 27 further comprising a wire coil surrounding said durable segment.

* * * * *